United States Patent [19]
Zelman

[11] Patent Number: 5,403,307
[45] Date of Patent: Apr. 4, 1995

[54] APPARATUS, SYSTEM, AND METHOD FOR SOFTENING AND EXTRACTING CATARACTOUS TISSUE

[76] Inventor: Jerry Zelman, 960 Arthur Godfrey Rd., Miami, Fla. 33140

[21] Appl. No.: 912,322

[22] Filed: Jul. 13, 1992

Related U.S. Application Data

[63] Continuation-in-part of Ser. No. 733,687, Jul. 22, 1991, Pat. No. 5,139,504, which is a continuation-in-part of Ser. No. 539,444, Jun. 18, 1990, Pat. No. 5,112,339, and a continuation-in-part of Ser. No. 245,144, Sep. 16, 1988, Pat. No. 5,057,098, which is a continuation-in-part of Ser. No. 44,544, May 1, 1987, Pat. No. 4,825,865.

[51] Int. Cl.$^6$ ............................................. A61B 3/00
[52] U.S. Cl. ............................................. 606/6; 606/4; 607/89
[58] Field of Search .................. 606/4, 5, 6; 128/395, 128/396, 399, 397; 607/50, 53, 90, 91, 92, 93, 89

[56] References Cited

U.S. PATENT DOCUMENTS

| | | |
|---|---|---|
| 3,315,680 | 4/1967 | Silbertrust et al. ............... 606/4 X |
| 4,309,998 | 1/1982 | Aron Nee Rosa . |
| 4,477,179 | 10/1984 | Mizuno et al. ................... 128/397 X |
| 4,520,816 | 6/1985 | Schachar . |
| 4,582,405 | 4/1986 | Muller et al. ....................... 606/6 X |
| 4,758,081 | 7/1988 | Barnes ................................... 606/4 |
| 4,825,865 | 5/1989 | Zelman . |
| 5,057,098 | 10/1991 | Zelman . |
| 5,098,426 | 3/1992 | Sklar . |
| 5,112,339 | 5/1992 | Zelman . |
| 5,139,504 | 8/1992 | Zelman . |

FOREIGN PATENT DOCUMENTS 2143052 1/1985 United Kingdom ................... 606/4

*Primary Examiner*—Sam Rimell
*Attorney, Agent, or Firm*—Cushman, Darby & Cushman

[57] ABSTRACT

A laser may be used to soften the cataractous tissue prior to removal with the wedge-tipped probe. The cataract softening or other laser energy used during the surgical procedure being performed may be delivered through the operating microscope. In the case of cataract softening, when the laser is so delivered, no delay is required between cataract softening and cataract removal.

2 Claims, 6 Drawing Sheets

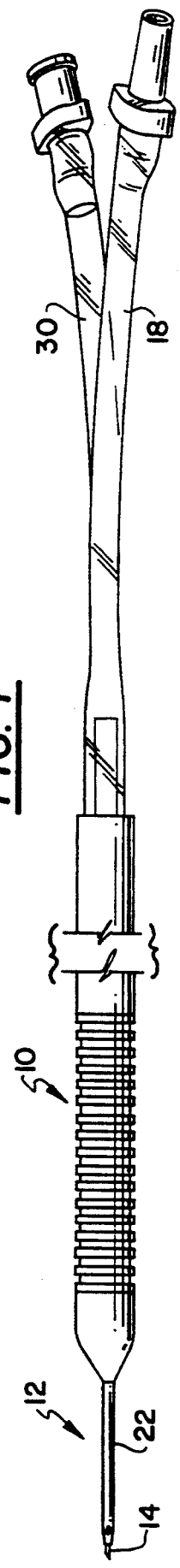
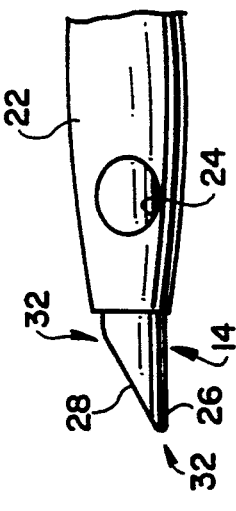
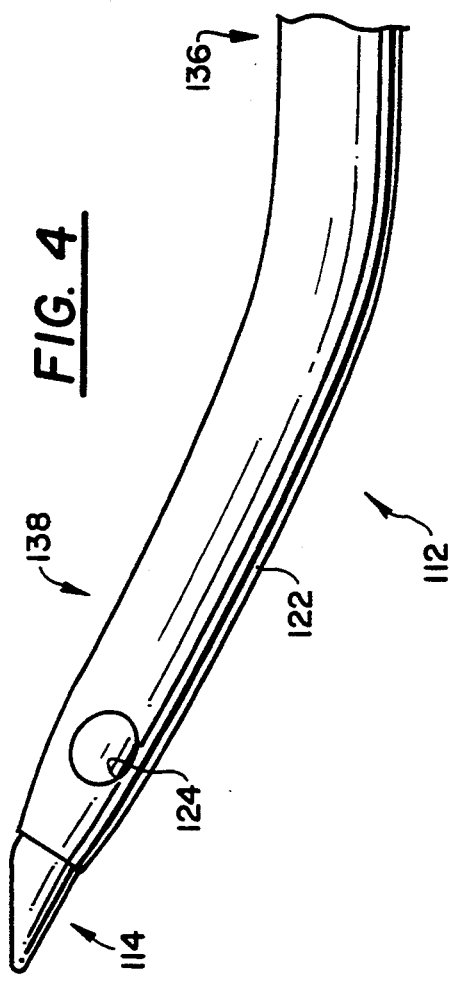

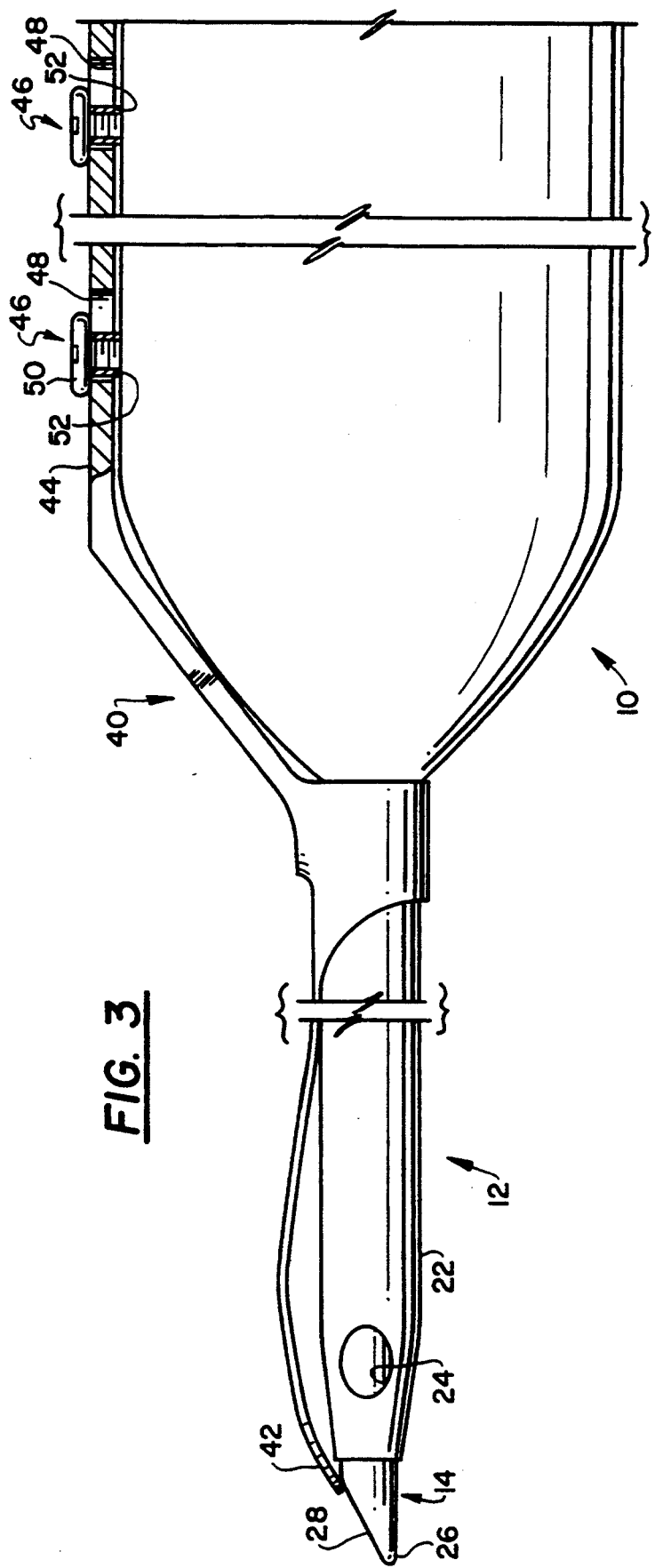

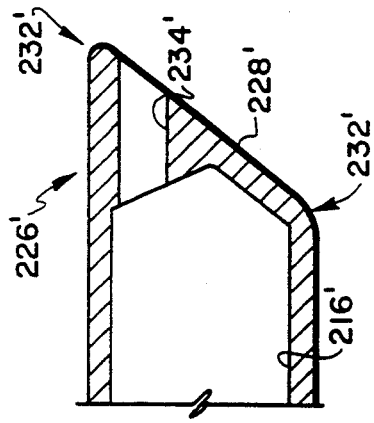
FIG. 10
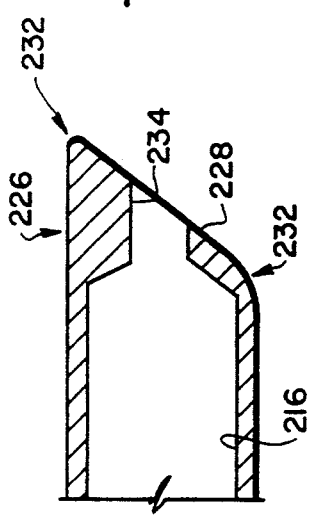
FIG. 9
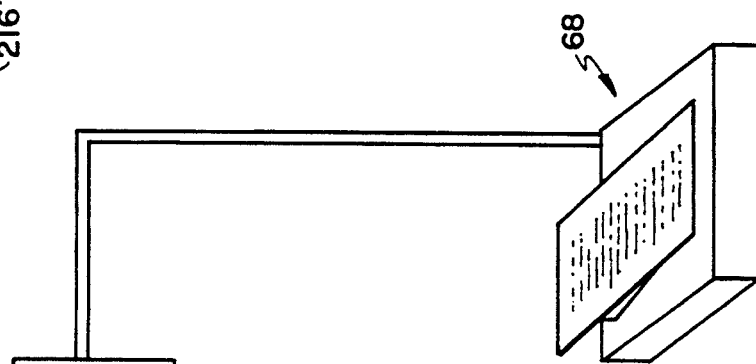
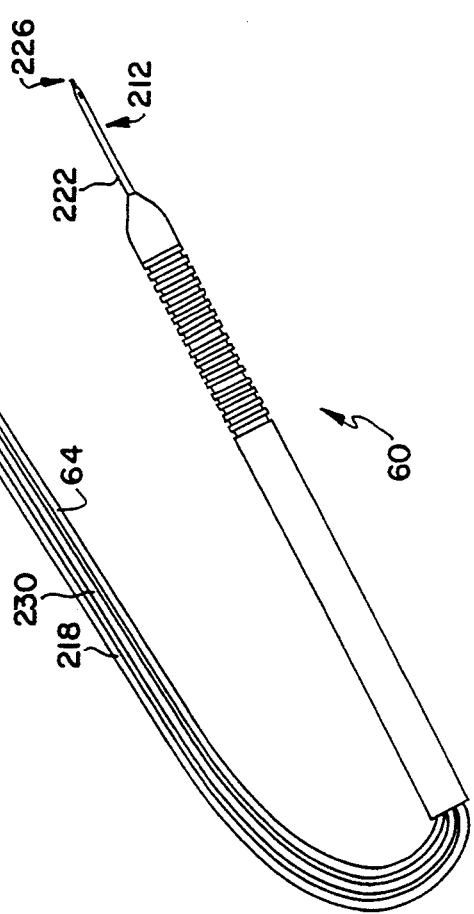
FIG. 8

APPARATUS, SYSTEM, AND METHOD FOR SOFTENING AND EXTRACTING CATARACTOUS TISSUE

The present invention is a continuation-in-part of U.S. application Ser. No. 07/733,687, filed Jul. 22, 1991, now U.S. Pat. No. 5,139,509, which was a continuation-in-part of U.S. application Ser. No. 07/539,444, filed Jun. 18, 1990, and now U.S. Pat. No. 5,112,339, and a continuation-in-part of U.S. application Ser. No. 07/245,144, filed Sep. 16, 1988, and now U.S. Pat. No. 5,057,098, which was a continuation-in-part of U.S. application Ser. No. 07/044,544, filed May 1, 1987, and now U.S. Pat. No. 4,825,865.

BACKGROUND OF THE INVENTION

1. Field of the Invention

The present invention relates to apparatuses for extracting cataractous tissue and, in particular, to wedge-shaped probes for phacoemulsification, for removal of soft cataractous tissue, and for cortical clean-up.

2. Description of the Related Art

The human eye includes an anterior chamber and a posterior chamber which are separated by a normally transparent lens which performs the function of focussing light onto the retina defined along the rear wall of the posterior chamber. The lens can become cloudy for any of a variety of reasons which results in the impairment of vision. The cloudy lens must then be removed and replaced with an intraocular lens (IOL) implant. In the alternative, thick glasses or contact lenses can be used to properly focus light onto the retina.

Many techniques are now used for removing the cloudy, cataractous lens material. One of those techniques is phacoemulsification. With this technique a small incision is made in the surface of the eye and a probe is inserted through that incision. The probe will typically include an irrigation passage for conveying irrigating fluid into the eye and an aspiration passage for removing cataractous tissue and the irrigating fluid from within the eye. The probes are coupled to a source of ultrasonic power and ultrasonic vibration is selectively applied to the probe to break up cataractous tissue which the probe contacts to facilitate aspiration of the same.

One significant advantage of phacoemulsification is that the incision in the eye can be smaller than with some other cataract lens removal techniques. There are numerous benefits to small incision surgery including small wound size, less post operative astigmatism, more controlled removal of cataractous material, earlier recovery of visual function and early ambulation of the patient.

One difficulty with phacoemulsification is that considerable problems are often encountered in mastering the skills needed to perform the procedure safely. However, even after the surgeon has become skilled in the phacoemulsification technique itself, conventional phaco handpieces present a number of difficulties which skill alone cannot remedy.

More particularly, conventional phacoemulsification probes are typically in the form of an elongated tube which terminates distally in a sharp planar end or a sharp pointed or sloped end. That tube defines the aspiration passage for removing cataractous tissue and fluid from within the eye. Thus, the aspiration port and passage have a diameter defined by the diameter of the tube, which is typically relatively large, on the order of 2 to 3 millimeters, and the aspiration passage has a generally constant bore along its entire length.

Irrigation fluid is typically provided via an irrigation sleeve provided in surrounding relation to the sharp tube for supplying the irrigation fluid to the interior of the eye. When the handpiece is in use, fluid flows through the irrigation line, through the eye and through the large bore aspiration port. This makes the system inside the eye very susceptible to any kind of fluctuation in irrigation supply and aspiration pressure. Indeed, a drop in irrigation supply or sudden increase in aspiration pressure can result in collapse of the eye because such a large bore is disposed within the eye. In addition, there is a risk that vital structures of the eye, not just cataractous tissue, will enter the large aspiration passage. Yet a further problem associated with such large bore conventional phaco probes is that material which is sucked into the constant bore aspiration passage can become clogged within the probe, requiring that the probe be removed from the patient's eye to be cleared.

Conventional phaco probes have a relatively low maximum aspiration level, approximately 60 mmHg, because of their relatively large aspiration port and the attendant risk of collapse. With such a vacuum level, it is difficult for conventional phaco probes to efficiently aspirate cataract material to the tip and hold it there while the ultrasonic vibration of the probe emulsifies it. Rather, the aspiration pressure tends to draw the cataract material towards the probe, but the ultrasonic vibration of the probe tends to push the cataract material away from the tip. These antagonistic forces make it very difficult for the practitioner to quickly and efficiently remove cataract material from within the eye. In addition, because phaco probes typically have a thin sharp distal edge, there is a very small surface area through which ultrasonic energy can be transmitted to the cataractous tissue. As a result of the size of conventional phaco probe aspiration ports, the low vacuum level and the small distal surface area, ultrasonic energy must be delivered to the probe for a relatively long period of time and at a high energy level to break up the cataractous material.

Furthermore, because of their sharp distal edges, conventional phaco probes present a significant risk of damage to the cornea, iris, and posterior capsule when inserted into the eye. This risk is increased several fold when ultrasonic energy is applied to the tip of the probe.

Thus, conventional phaco probes have a configuration which requires the lengthy application of high ultrasonic energy to break up cataractous tissue. However, the configuration of conventional probes also requires that the application of ultrasonic energy be minimized in power and duration to protect the eye from damage which can be caused by movement of the sharp tip of the probe within the eye.

The sharp tip and large bore provided on conventional phaco probes make these probes unsuitable for removal of the softer cortex of the cataract material. Thus, conventionally, phaco probes have been used to remove the harder nucleus of the cataract material and an irrigation/aspiration handpiece is used instead to remove the softer cortex of the cataract material. Such conventional irrigation/aspiration handpieces are typically rounded end probes with a hole in a top surface thereof for nudging the cortical material and aspirating the same. Such irrigation/aspiration handpieces have the disadvantage that it is difficult to direct material to be aspirated to the aspiration opening and, of course, the distinct structure and purpose of the irrigation/aspiration handpiece and the phaco probe require that two separate instruments be inserted into the eye to complete the cataract removal procedure.

Laser radiation has been used for the past several years to ablate various tissues within the eye. For example, the use of a ND:YAG laser (hereinafter referred to by the more common term, YAG laser) to remove abnormal and normal tissue has been explored. See, e.g., U.S. Pat. No. 3,971,382 to Krasnov, U.S. application Ser. No. 06/702,569 filed Feb. 19, 1985 and an article by William Steven Chambles entitled *Neodymium: YAG Laser Anterior Capsulotomy and a Possible New Application*, (AM Intra-Ocular Implant Society Journal, Vol. 11, January 1985). Furthermore, it has been generally recognized that laser radiation, particularly from a YAG Laser, will soften cataract tissue. However, one of the difficulties with the use of laser radiation to soften cataract tissue is that fragments of the tissue are often too large or otherwise dimensioned to prevent ready passage through an aspiration opening in a probe such as used in phacoemulsification. In order to avoid making an incision which is undesirably large, that is more than the desired 2.5 to 3.5 mm, the aspirating opening must necessarily be quite small and the dimensions of the path within the probe to the vacuum source are similarly restricted. For that and other reasons, the use of laser radiation to soften cataracts for subsequent aspiration has not been practical as a standard surgical procedure.

SUMMARY OF THE INVENTION

It is therefore an object of this invention to provide a probe which does not have a sharp distalmost end so that the likelihood that structures within the eye will be damaged, particularly when the probe is vibrated will be minimized.

It is also an object of this invention to provide a probe which minimizes or eliminates the need for the application of ultrasonic energy to break up cataractous tissue.

It is yet a further object of this invention to provide a probe wherein higher aspiration levels can be provided, that is pressures sufficient to draw the cataractous tissue to the aspiration port, even when ultrasonic energy is being applied.

A further object of this invention is to provide a handpiece which minimizes the likelihood that cataractous material will clog the aspiration passage.

Another object of this invention is to provide probes which may be used for both removal of the harder nucleus of the cataract material and cortical clean up so that two probes need not be sequentially inserted into the eye to complete the cataract removal procedure.

Yet another object of this invention is to provide a number of probes which may be used to train a surgeon to perform small incision cataract removal surgical procedures, each probe having the same or a similar basic configuration but each is accessorized so as to accommodate the skill and expertise of the surgeon and the procedure to be performed.

Thus, it is an object of the present invention to provide apparatuses and specifically probes for the removal of cataractous lens tissue which overcome the problems associated with the prior art phaco handpiece and the irrigation/aspiration handpiece noted above.

It is yet a further object of the invention to provide an apparatus, system and method which advantageously applies a beam of laser radiation to cataractous tissue to be removed to soften the same and then makes possible facile removal of the thus softened tissue.

On the one hand, the invention resides in the provision of a wedge-shaped irrigation/aspiration handpiece for the removal of cataractous tissue from within the eye. The wedge-shaped irrigation/aspiration handpiece has polished distalmost edges so that there are no sharp edges, i.e. the edges are blunt, and hence the risk of damage to the cornea, iris or posterior capsule when the probe is used is minimized. Furthermore, the sloped-shape of the probe tip permits effective scooping of cataract material within the eye. Likewise the wedge shape efficiently lifts cortical material off the posterior capsule and is useful for posterior capsule clean-up. Thus, the irrigation/aspiration handpiece of the invention can be used for cortical clean-up. The handpiece can also be used to remove soft cataract material without using ultrasound. Preferably, when the instrument is used for that purpose, a movable spatula element is provided for crushing material which becomes lodged in the aspiration opening so as to keep that opening clear for aspirating cataractous material.

The invention further resides in the provision of a probe for use in phacoemulsification. Like the wedge-shaped irrigation/aspiration handpiece, the phaco probe of the invention has a polished smooth, wedge-shaped forward end to facilitate directing material to the aspirating opening and to minimize risk to surrounding tissue. The phaco probe of the invention is further characterized in that a small bore aspiration port is defined in the distalmost sloped end face of the probe. By decreasing the aspiration port size, higher aspiration levels can be used to draw cataract material to the tip and to obtain a good emulsification action. Because a small bore is used, the system is not nearly as susceptible to fluctuations in irrigation or aspiration pressure as large bore systems. Thus providing a small port, from an electromechanical standpoint makes the procedure much more controlled, gives better draw of the cataract material to the tip and is less susceptible to changes in pressures and vacuums within the eye.

A further advantage of the small bore port and wedge-shaped phaco probe of the invention is that a greater surface area is defined at the tip of the probe. A wider surface area ensures that the maximum cavitation energy from the ultrasonic vibration is applied to the cataractous material itself to break-up the same and thus reduces the required power levels for efficient phacoemulsification. Thus the device of the invention works well at low powers which means less turbulence will be generated within the eye, there is less movement of the tip with respect to the cataract material and it is less likely that the probe will encounter the delicate tissues of the eye.

A movable spatula element may also be mounted to the small port phaco probe of the invention so that it can be used to remove cataractous tissue without using ultrasound so that in the event cataractous tissue becomes lodged in the aspiration port it can be disrupted with the spatula.

The present invention even further relates to a unique method which resolves the above-noted problems with softened cataractous tissue and makes practical the use of laser radiation to soften and eventually fragment cataract tissue which can then be removed through an instrument inserted through a 2.5-3.5 mm incision in the surface of the eye. According to the present invention, fragments, which do not pass readily through the aspiration opening may be dislodged. In one embodiment of the invention, some vibration can be applied to the instrument to encourage passage of the tissue into the probe. In the alternative, the spatula element which may be mounted to the probe in accordance with the invention is urged to contact and break-up such lodged fragments. The smaller fragments resulting are then sucked through the aspiration opening. In yet a further embodiment, a small port bore configuration is provided so that maximal aspiration can be applied to ensure that the cataract tissue will be aspirated without collapsing the eye.

In certain instances, either because of the logistics of the operating room, as noted below, or because of the needs of a particular patient, a waiting period of hours or days following laser softening may be desirable. However, in some instances, such a waiting period is not desirable because it is a period during which complications to the laser softening can occur.

Heretofore, when laser energy has been delivered to a cataract for the purpose of softening the cataract, a slit lamp has been utilized. Use of a slit lamp to deliver the laser energy necessitated a delay between the laser treatment and removal of the softened cataract of hours or days because of the logistics of the operating room. More particularly, slit lamps are used with the patient in a sitting-up position. If a patient is to undergo surgery, however, the patient is premedicated or has had a retrobulbar block performed. When the patient has been premedicated or has had a block done, it is difficult to have the patient in a sitting-up position to allow use of a conventional slit lamp. A slit lamp is known which tilts downward so as to be used on a person who is laying down. However, even in that case one still needs to move the operating microscope into position and thus two devices are required, which can interfere with the procedure.

In accordance with the present invention, a laser procedure is provided wherein it is not necessary for the patient to be in an upright, seated position and, thus, the laser procedure can be performed after peribulbar or retrobulbar anesthesia have been administered, the patient's pupil has been dilated, and the surgical pre-op has been performed, and it is not necessary to wait a period of hours or days following laser softening to complete the cataract removal procedure. In addition, in accordance with the invention, a completely separate device for the laser procedure is unnecessary. To that end, in accordance with the invention the laser energy is delivered through a fiber optic cable and/or a system of mirrors through the operating microscope and focused, desirably with the focusing mechanism of the microscope, into the nucleus of the cataract. In the case of a YAG laser beam, which is invisable, a HeNe laser is used for aiming and focusing. The focused laser energy can also be used to perform an anterior capsulotomy on the cataract. If necessary or desirable to conduct the laser light from the microscope to the eye, a fiber optic cable/probe of known design may be provided. The phaco and/or aspiration of the softened cataract can be performed immediately after the laser softening. Advantageously, the phaco and/or aspiration of the softened cataract is performed with the phaco needle and/or hand piece disclosed and illustrated herein.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

FIG. 1 is an elevational view of a irrigation/aspiration handpiece provided in accordance with the present invention;

FIG. 2 is an enlarged elevational view of the forward portion of the handpiece of FIG. 1;

FIG. 3 is an enlarged elevational view of an alternate embodiment of the present invention;

FIG. 4 is an enlarged elevational view of the forward portion of a handpiece in accordance with a further embodiment of the invention;

FIG. 8 is a schematic perspective view of a small port phaco device provided in accordance with the present invention;

FIG. 9 is a cross-sectional view of the tip of the small port phaco probe in accordance with the present invention with the irrigation sleeve omitted for clarity;

FIG. 10 is a cross-sectional view of an alternate tip of a small port phaco probe in accordance with the present invention with the irrigation sleeve omitted for clarity;

DETAILED DESCRIPTION OF THE PRESENTLY PREFERRED EXEMPLARY EMBODIMENT

Figure 6:
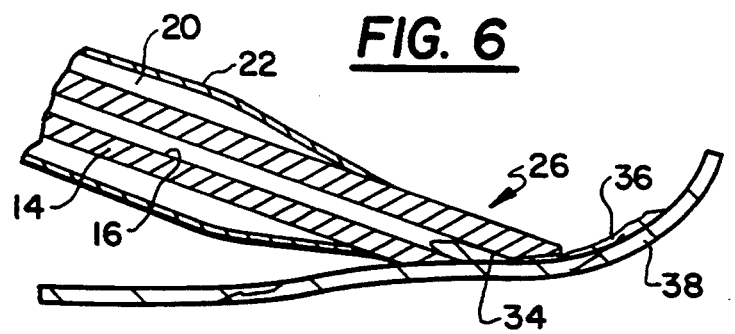
FIG. 6 is an enlarged schematic cross-sectional view showing the use of the handpiece of FIGS. 1 and 2 in accordance with the invention.

An irrigation/aspiration handpiece in accordance with the present invention is shown by way of example in FIGS. 1 and 2, and 6.

The handpiece includes a main body portion 10 adapted to be gripped by the surgeon's hand and a probe portion 12 extending along the longitudinal axis of the main body portion 10 and from a distal end thereof. The probe portion 12 includes a tubular element 14 defining an aspiration passage 16 (FIG. 6) which is operatively coupled to an aspiration passage (not shown) defined within the main body portion 10. A flexible tube 18 is provided at the proximal end of the aspiration passage of the main body portion 10 for interconnecting that passage to a source of suction.

An irrigation passage 20 (FIG. 6) is further provided in accordance with the present invention. In the illustrated embodiment a sleeve 22 is defined in surrounding relation to the tubular element 14, The irrigation passage 20 is defined between the sleeve 22 and the tubular element 14. Irrigation openings 24 (only one of which is shown for clarity) are preferably defined through the sleeve 22 adjacent the distal end of the probe 12 on each lateral side thereof. In this manner, when the sloped surface 28 of the wedge tip 26 is in engagement with cataractous tissue, as discussed more fully below, irrigation fluid will be allowed to flow to the surgical site. An irrigation passage (not shown) is also defined through the main body portion 10 and operatively coupled to the irrigation passage 20 in the probe 12 when the probe 12 is mounted to the main body portion 10. A flexible tube 30 is mounted to the proximal end of the irrigation passage of the main body portion 10 for interconnecting that passage to a source of irrigating fluid.

As shown in FIG. 2, the irrigation passage defining sleeve 22 terminates proximally at the distal end of the tubular element 14. The tubular element 14 on the other hand terminates distally in a wedge-shaped tip 26. The tip is preferably configured so that the sloped face 28 of the tip 26 is disposed at an angle of between about 25 and 50 degrees with respect to the longitudinal axis of the tubular element 14 and most preferably at an angle of between about 30 and 45 degrees. It is to be understood, however, that the particular disposition of the wedge-shaped tip would depend upon the nature and age of the cataract and the procedure being performed, as well as whether or not ultrasound and/or the spatulated tip of the invention, described more fully below, are being used.

The wedge-shaped tip 26 is polished as at 32 so that there are no sharp edges. The smooth, blunt and rounded edges minimize the risk of damage to the cornea, iris or posterior capsule when the handpiece is used. Further, in accordance with a preferred embodiment of this invention, the distalmost aspiration opening 34 which is defined through the sloped distal face 28 of the tubular element 14 is on the order of 0.2 to 0.6 millimeters in diameter, and most preferably 0.3 to 0.4 millimeters in diameter. Further, the opening preferably opens into a larger aspiration bore within the tubular element, on the order of about 2.0 to 3.0 millimeters, so as to minimize the likelihood that the probe 12 will become clogged with cataractous tissue and to maximize the aspiration level which can be applied through the probe 12 as described more fully below with reference to FIGS. 8-10.

As noted above, the polished edges 32 of the wedge-shaped tip will minimize the likelihood that the probe will damage the eye during the cataractous lens removal procedure. Furthermore, the shape of the tip 26 and surface area defined by the sloped end face 28 in surrounding relation to the aspiration port 34 permits effective scooping of the cataractous tissue to direct the same towards the aspiration opening. More particularly, as shown by way of example in FIG. 6, the probe 12 in accordance with the invention efficiently lifts cortex 36 off the posterior capsule 38 and is useful for posterior capsule clean-up. The cataractous material encountered by the probe 12 during such a clean-up procedure is relatively soft and it is unlikely that cataractous tissue will become lodged in the aspiration bore 34. The likelihood of such obstruction is further diminished by the high aspiration levels which are possible at the distalmost bore, as noted more fully below with reference to FIGS. 8-10.

The embodiment of FIG. 4 is substantially similar to the embodiment illustrated in FIGS. 1, 2 and 6 and described with reference thereto. However, the irrigation/aspiration handpiece probe 112 depicted in FIG. 4 differs in that the tubular element 114 and irrigation sleeve 122 includes a proximal portion shown generally at 136 and a distal portion shown generally at 138 which is disposed at an angle of between 0 and 180 degrees with respect to the longitudinal axis of the proximal portion 136. The bent tip probe 112 may be preferred by some practitioners to minimizing obstruction of the surgical site, and for ease of manipulating the view probe during the procedure to properly locate the tip of the probe to remove the cataractous material.

Figure 5:
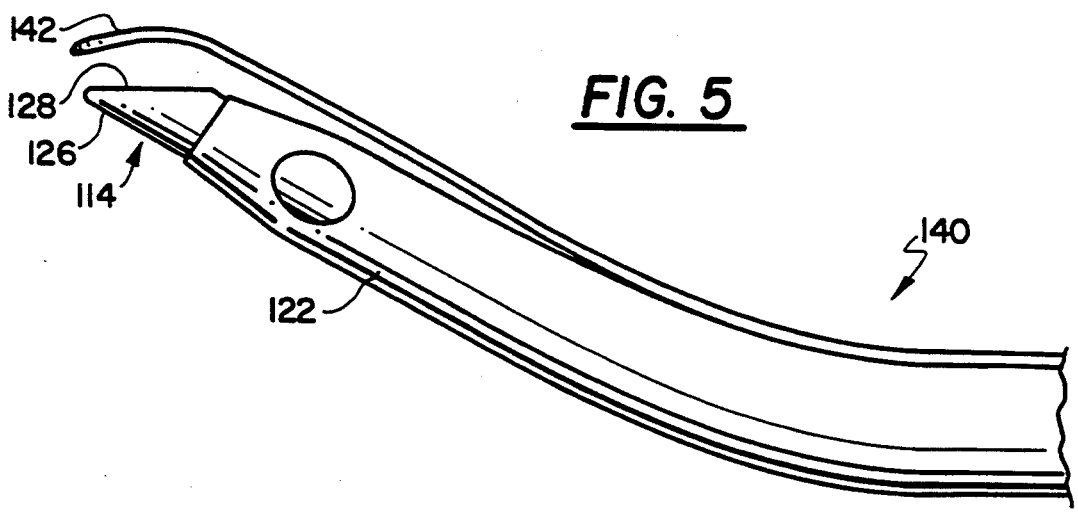
FIG. 5 is an enlarged elevational view of the forward portion of a handpiece in accordance with yet a further embodiment of the invention.

The embodiments FIG. 3 and 5 are substantially similar to the embodiments of FIGS. 1-2 and 6, respectively. However, in accordance with the embodiment to FIGS. 3 and 5, a spatula-like element 40, 140 is mounted in longitudinal sliding relation to the tip 12, 122 of the handpiece.

The spatula-like element 40, 140 includes a spatula tip 42, 142 which is disposed at an angle with respect to the axis of the distal portion of the tubular element 14, 114 which substantially corresponds to the angle at which the inclined face 28, 128 of the wedge tip 26, 126 is disposed.

As shown in FIG. 3, the proximal, control portion 44 of the spatula-like element 40 is mounted in parallel sliding relation to the body 10 of the handpiece so that it can be engaged and moved by the practitioner finger(s). While the control portion 44 of the spatula-like element 40 can be mounted to the main body portion 10 in any suitable manner which allows longitudinal movement of the same, in the illustrated embodiment, first and second projections 46 are defined which extend radially outwardly from the surface of the handpiece and through corresponding slots 48 defined in the control portion 44 of the spatula-like element 40. The radially outermost ends of the projections are enlarged as at 50 to maintain the control portion 44 adjacent the body 10 of the handpiece. Thus, the projections 46 can be defined by screws threaded into corresponding apertures in the main body portion for ease of assembly. Preferably sleeves 52 are defined in surrounding relation to such threaded projections 46 to limit the penetration of the same into the main body portion 10 to ensure the spatula-like element 44 will be slidable with respect thereto. The slots 48 are defined longitudinally of the control portion 44 so as to allow limited longitudinal movement of the spatula-like element 44.

Figure 7A:
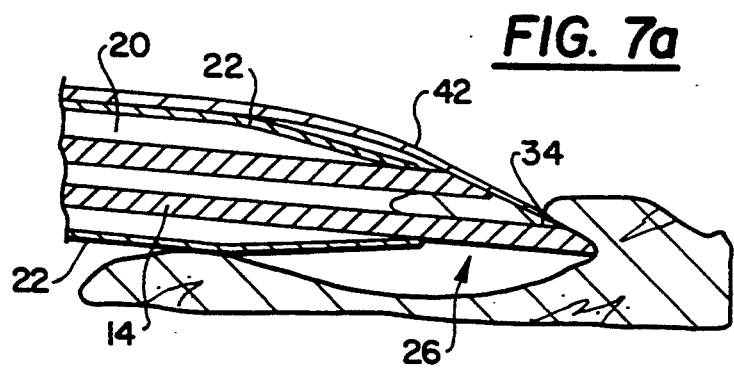
FIGS. 7a and 7b are enlarged schematic cross-sectional views of the handpiece of FIG. 3 showing the use of the spatula provided in accordance with the present invention.
Figure 7B:
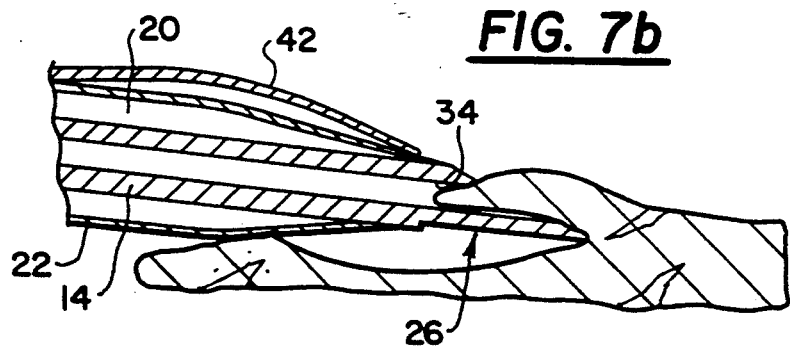

In accordance with the preferred embodiment of the invention, the slots are defined so that movement of the control portion 44 in a forward direction to a forwardmost position wherein the projections 46 engage the rearwardmost ends of the slots 48 causes the spatula tip 42 to extend forwardly beyond the inclined surface 28 of the wedge tip 26. Movement of the control portion 44 rearwardly from that forwardmost position causes the spatula tip 42 to first come into contact with the sloped surface 28 of the wedge tip 26 and then slide upwardly and rearwardly with respect to that surface to a maximum retracted position wherein the spatula tip is disposed at the rearwardmost edge of the sloped surface of the wedge tip (FIGS. 2 and 7b). The maximum retracted position is preferably defined by engagement of the projections 46 with the forwardmost ends of the slots 48.

Thus as shown in FIG. 7b, the spatula tip 42 can be moved to a position rearwardly and away from the aspiration opening 34 so that cataractous tissue can be scooped and aspirated without obstruction. If cataractous tissue becomes lodged in the aspiration opening 34 and it is necessary for this material to be dislodged, the spatula-like element is advanced forwardly so the tip is moved, as shown in FIG. 7a, into engagement with the cataractous tissue which has become lodged in the aspiration opening 34. Movement of the spatula tip 42 with respect to the wedge-shaped tip 26, as discussed above, effectively dislodges any material. Thus, when the instrument is utilized to remove a soft cataract through a small incision but without using ultrasound, the embodiment of the invention including a movable spatula element 40, 140 as shown in FIGS. 3 and 5 is preferably employed so that the spatula element can be used for crushing material which becomes lodged in the aspiration opening to keep that passage clear for aspiration.

If the cataractous tissue is too hard to aspirate using the spatulated instrument of FIGS. 3 and 5 without ultrasound, it is very simple to convert the procedure. Thus, for example, if the handpiece is operatively coupled to a source of ultrasonic energy, when such hard, uncrushable material is encountered the probe can be used to phacoemulsify the same.

The spatulated wedge device can also be used as an adjunct to standard phacoemulsification. Specifically, after removal of most of the nucleus of the cataract material with a phaco probe, the remaining rim of nucleus and cortex, which is difficult to remove with a standard phaco tip, can be removed using the spatulated handpiece of the invention. Indeed, the spatula element allows the remaining harder cataract material to be crushed and aspirated and the posterior capsule to be cleaned up.

As noted above, a wedge-shaped handpiece in accordance with the present invention having a source of irrigation fluid and a source of aspiration suction operatively coupled thereto can be used for cortical clean up. It is unnecessary to provide any means for dislodging material from adjacent the aspiration opening when such soft cataractous material is removed. When the instrument is utilized to remove soft cataractous material through a small incision other than during cortical clean up, but without using ultrasound, the embodiment of the invention including a movable spatula element for crushing material which has become lodged in the aspirating opening can be utilized and is sufficient to remove the soft cataractous material.

In accordance with the further aspect of the invention, however, a phaco handpiece 60 is provided which enables the removal of the relatively hard cataract material. As shown in FIG. 8, the phaco handpiece of the invention differs from the irrigation/aspiration handpiece primarily in that means 64 are provided for coupling the probe 212 to a source of ultrasonic energy such as a phacoemulsification machine 66 so that the tip 226 can be vibrated to emulsify cataractous material which comes into contact therewith.

Thus, in accordance with the invention, the phaco probe has substantially the same wedge-shaped tip 226, with an irrigation sleeve 222 and an aspiration opening 234 defined in the inclined face 228 of the wedge-shaped tip 226, and with polished edges as at 232 to minimize damage should the instrument come into contact with the structure of the eye. Likewise, means 218 and 230 are provided for coupling the main body portion 210 respectively to sources of aspiration suction and irrigation fluid such as the phacoemulsification machine 66.

The particularly unique aspect of the phaco tip 226 of the invention is the provision of a small aspiration port 234 on the order of 0.2 to 0.6 mm, and most preferably 0.4 mm. As shown in FIGS. 9 and 10, the small port 234, 234' defined in the phaco tip in accordance with the present invention opens up into an aspiration passage 216, 216' substantially corresponding in diameter to conventional phaco probe aspiration bores. Thus, the aspiration passage 216, 216' proximal of the distal port 234, 234' has a diameter of between about 2.0 and 3.0 mm, for example, on the order of 2.5 mm. Providing such a small port allows the surgeon to select aspiration levels of up to 550 mmHg. Indeed, the small size of the port allows such high aspiration levels to be utilized without causing collapse of the eye or undesired aspiration of ocular tissues because it is less sensitive to fluctuations in irrigation or aspiration pressures.

In the embodiment shown in FIG. 9, the small port aspiration opening 234 is defined centrally of the inclined face 228 of the wedge tip 226. In the alternative, however, as illustrated in FIG. 10, the small port 234' can be provided off-center, spaced proximally or distally, as shown. The ideal location for the small port, of course, depends upon the procedure being performed, the nature of the cataractous material and the requirements of the surgeon.

The phaco probe of the invention preferably utilizes on/off irrigation, linear aspiration and phaco on demand controlled by for example a foot pedal 68. The combination of the wedge shape and high aspiration levels allows a surgeon to scoop up and aspirate soft pieces of cataract material. The harder particles of cataract material are also conveniently scooped up by the wedge and are then held in place with the high aspiration levels. Phacoemulsification is effected by moving the foot pedal to the side to activate ultrasound energy. The intensity of the ultrasound energy is preselected by the surgeon and the ultrasonic energy is delivered as long as the foot pedal is held to the side and sufficient for phacoemulsifying particles of cataract material. Because of the high aspiration levels which can be delivered to the cataractous tissue through the aspiration passage and port, the hard pieces of cataract are effectively held in place on the inclined face of the probe so that the ultrasonic energy is effectively delivered to the cataractous material and the cataractous material is quickly emulsified thereby. Further, because in accordance with the invention, the sloped end face of the probe itself has a relatively great surface area in contact with the cataractous tissue, that tissue can be effectively emulsified with a minimum amount of ultrasonic energy. While a foot pedal has been mentioned as a means for controlling the ultrasonic energy, of course any known control device or means could be used to control the application of ultrasonic energy.

Thus the provision of the small port in accordance with the invention enables the cataractous tissue to be held closely against the tip of the probe and minimizes the ultrasonic energy that must be applied via the probe, thus increasing the control that the surgeon has of the probe. After the nucleus of the cataract material has been removed, cortical clean-up can be performed with the same phaco handpiece. Indeed, it is not necessary to exit the eye and re-enter with an irrigation/aspiration handpiece. Rather, the phaco probe of the invention can be utilized without ultrasonic power to perform cortical clean-up in a manner analogous to that described with reference to FIG. 6.

As is apparent from the foregoing, the wedge-shaped small port phaco device and procedure in accordance with the invention allows delivery of ultrasound power to be kept to a minimum thus reducing the risk of complications.

The small port bore in accordance with the present invention also has the significant advantage that it eliminates the potential for clogging anywhere in the system. More particularly, the very small port of the inventive device opens up into a larger bore. Thus if material is aspirated through the small port, particularly under very high pressure, it will be capable of being aspirated through the bore of the remainder of the probe and the handpiece itself, which is on the order of ten times the size of the small bore itself. In conventional phaco aspiration probes, where the port and bore were of uniform diameter along the entire length of at least the probe, clogs could form in the probe or downstream because of restrictions in the line. Indeed, there was the potential for a clog anywhere the diameter of the flow passage decreases. In accordance with the present invention, however, the smallest opening, the port, is at the surface of the phaco device and that bore is enlarged all the way down the system. Thus there is no chance for the aspiration passage to become occluded.

The wedge-shaped handpiece of the invention is adapted for use with an irrigation/aspiration or phacoemulsification machine. The wedge-shape of the tip and polished slightly rounded edges allow efficient scoop up of adherent cortical material as well as the nucleus of the cataract material while minimizing the risk of damage to the delicate structures of the eye. The provision of a spatulated element in accordance with the embodiments of FIGS. 3 and 5 permits any cataractous fragments that become lodged in the aspiration port during the procedure to be crushed and thus allows the surgeon to use a handpiece which does not employ ultrasonic energy and thus does not have the risks attendant to the use of ultrasound power. As an alternative to or in addition to providing a spatulated element, the wedged-shaped handpiece of the invention shown in FIGS. 1-7 can be operatively coupled to a source of ultrasonic energy so that cataractous tissue which engages the distalmost tip of the probe can be emulsified and aspirated. Likewise, while the phaco device of FIGS. 8-10 has been described without reference to a spatula-like element, it is to be understood that to supplement the function of the ultrasonic energy or to provide a selective alternative thereto, the spatula-like element described with reference to FIGS. 3 and 5 could be mounted on the phaco probe in accordance with the invention.

Figure 11:
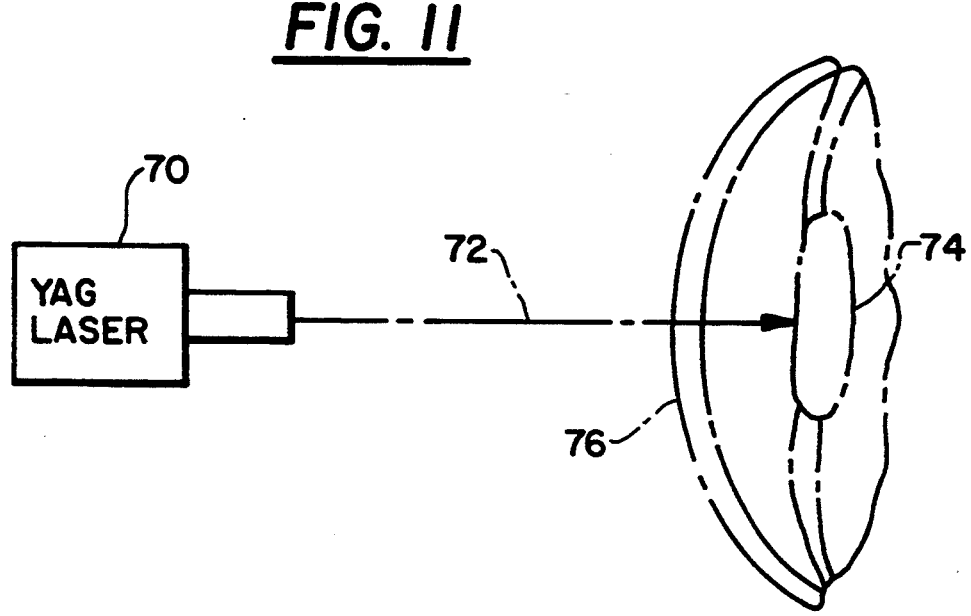
FIG. 11 is a schematic view of the application of laser radiation from, for example, a YAG laser to soften the cataract tissue.

In accordance with the invention, any of the inventive probes can be used in conjunction with a laser for softening the cataractous tissue. Thus, as schematically shown in FIG. 11, a laser 70 applies a beam 72 of radiation to a clouded lens 74 in the eye 76. By way of example, a conventional YAG laser using bursts of 3 mJ to 5 mJ focused on the center of the nucleus has been shown to provide satisfactory softening. More particularly, in an exemplary procedure, at least 50 laser bursts can be first applied to the posterior aspect of the nucleus at 3 mJ. Another 100 to 150 shots of 5 to 7 mJ can then be applied to the center of the nucleus. Removal can be immediately following softening or, a considerable time, even a week or more may pass between softening of the cataractous tissue and removal with the probe of the invention. As an alternative to using a YAG laser, an Eximer laser may be employed.

In certain instances, either because of the logistics of the operating room or because of the needs of a particular patient, a waiting period of hours or days following laser softening may be desirable. However, in some instances, such a waiting period is not desirable because it is a period during which complications to the laser softening can occur.

In accordance with a further aspect of the present invention, a laser procedure is provided wherein it is not necessary to, although one can, wait a period of hours or days following laser softening to complete the cataract removal procedure. Thus, in accordance with the invention the laser procedure can be performed after peribulbar or retrobulbar anesthesia have been administered, the patient's pupil has been dilated, and the surgical pre-op has been performed. To that end, in accordance with the invention the laser energy is delivered through a fiber optic cable 106 fed through and/or the system of mirrors 108 within the operating microscope 100 and focused, desirably with a focusing mechanism within the microscope, into the nucleus of the cataract. In that regard, because the YAG laser beam is invisible a HeNe laser is provided for use in aiming the laser light. Because the operating microscope 100, not a slit lamp, is used, the patient can be in a supine, or any other position and thus does not need to be in a seated position, and only a single apparatus, which is a combination of the operating microscope and laser system, need be provided.

If necessary or desirable for the particular procedure to be performed, a fiber optic cable/laser probe may be coupled to the apparatus to conduct the laser light to the eye and to allow the surgeon to precisely control its delivery. Thus, the focused laser energy can also be used to perform an anterior capsulotomy on the cataract.

The phaco and/or aspiration of the softened cataract can be performed immediately after the laser softening. Advantageously, the phaco and/or aspiration of the softened cataract is performed with the phaco needle and/or hand piece disclosed and illustrated herein.

Figure 12A:
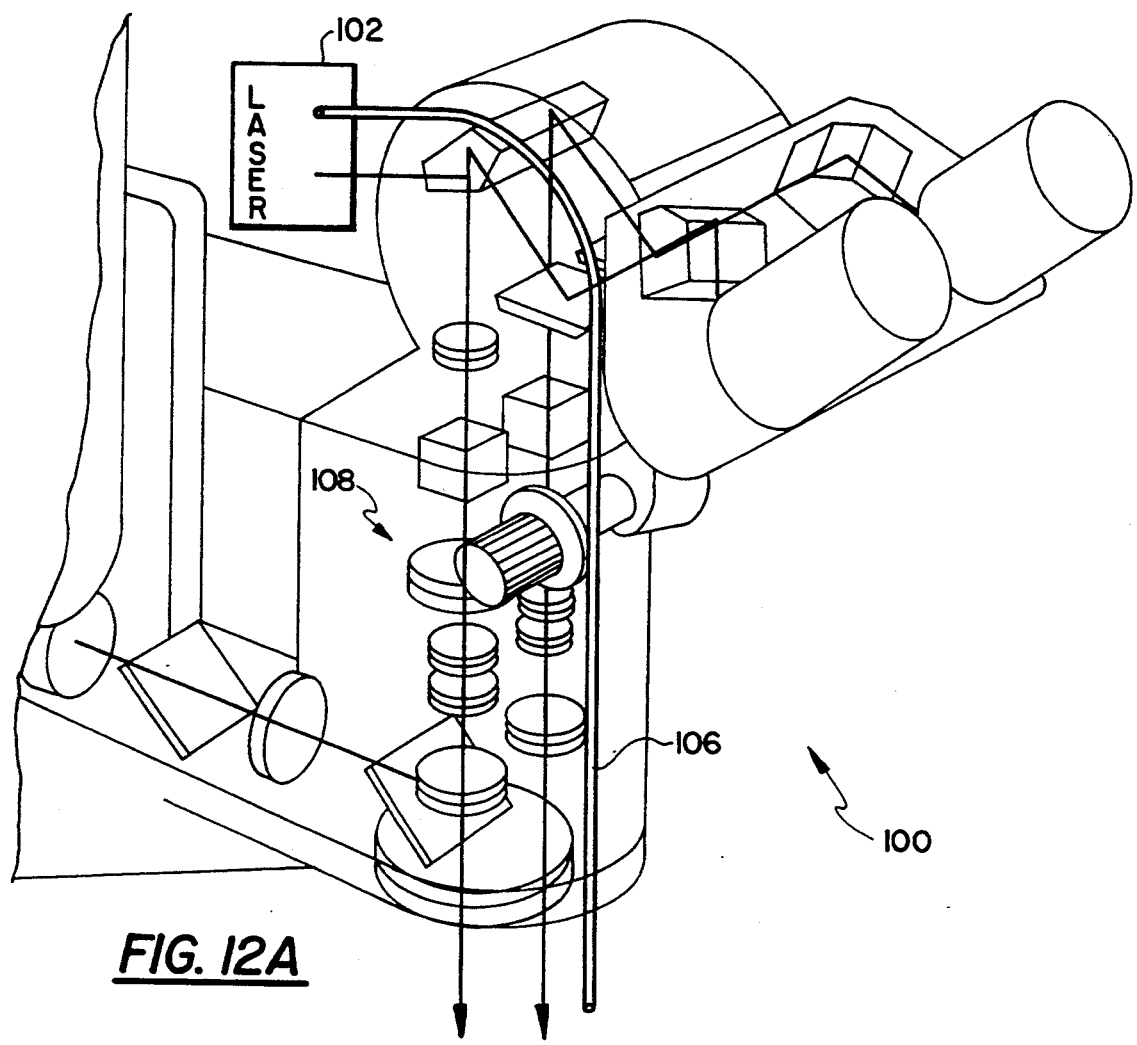
FIGS. 12A and 12B are schematic views of the application of laser energy through the operating microscope, in accordance with a further aspect of the invention.
Figure 12B:
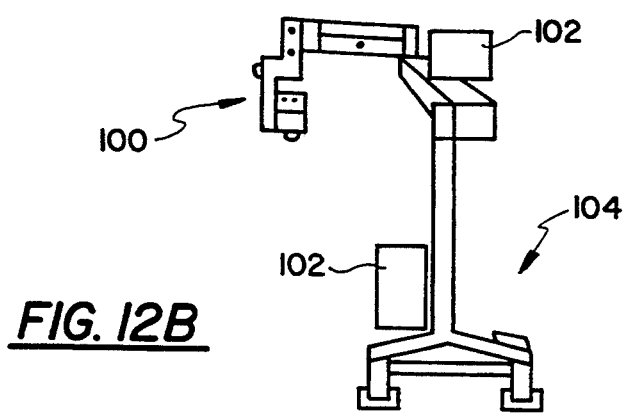

As shown in FIGS. 12A and 12B, the laser source 102 may be, for example, mounted atop or adjacent the base of the microscope support assembly 104. In accordance with the invention, the laser type and wave length may be selected depending upon the surgical procedure to be performed. Thus, the laser 102 can be selected so as to be capable of softening the hard nucleus of a cataract. In the alternative, where the laser energy is delivered through the operating microscope 100 into the cornea, the laser can be selected so that it can be focused to perform radial keratotomy incisions or corneal sculpting incisions. Such incisions change the contour of the cornea to cure of myopia, hyperopia and astigmatism.

When it is desired to remove the softened cataract, a small incision, for example on the order of 2.5 to 3.5 mm is made in the surface of the eye. The probe tube or needle is then inserted through the incision. The end of the probe is manipulated adjacent to the cataract tissue, which has already been softened and substantially fragmented by the prior application of laser radiation. The probe is then used as described above to remove the cataract tissue. If a fragment of tissue becomes lodged in the aspiration port, then the probe is vibrated, if coupled to a phacoemulsification machine, to dislodge and break up that fragment. In the alternative or additionally, if the probe has a spatulated tip in accordance with the invention, the spatula is advanced to contact, break up and/or dislodge the fragment.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A method of applying a laser one of to and into an eye during ophthalmic surgery comprising:

providing an operating microscope on a support structure;

mounting means for producing laser light to one of said operating microscope and said support;

generating a beam of laser light with said means for producing laser light;

directing said laser light from said source of laser light through said operating microscope;

providing a hand-held probe and a fiber optic cable for conducting said laser light to said hand-held probe, said fiber optic cable being operatively coupled to said hand-held probe and being operatively coupled to one of said source of laser light and said operating microscope; and impinging said laser light upon an eye.

2. A method as in claim 1, wherein said step of generating laser light includes generating a YAG laser beam and a HeNe laser beam.

* * * * *